United States Patent
Pflanz

(10) Patent No.: US 10,233,476 B2
(45) Date of Patent: Mar. 19, 2019

(54) APPARATUS AND METHOD FOR ANALYZING A CONTAMINATED SURFACE

(75) Inventor: Karl Pflanz, Gleichen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 0 days.

(21) Appl. No.: 13/702,428

(22) PCT Filed: Jun. 8, 2011

(86) PCT No.: PCT/EP2011/002794
§ 371 (c)(1),
(2), (4) Date: Dec. 6, 2012

(87) PCT Pub. No.: WO2011/160773
PCT Pub. Date: Dec. 29, 2011

(65) Prior Publication Data
US 2013/0089890 A1    Apr. 11, 2013

(30) Foreign Application Priority Data
Jun. 24, 2010    (DE) .................. 10 2010 024 933

(51) Int. Cl.
*C12Q 1/04* (2006.01)
*B01L 3/00* (2006.01)
(Continued)

(52) U.S. Cl.
CPC .............. *C12Q 1/04* (2013.01); *B01L 3/508* (2013.01); *C12M 23/10* (2013.01); *C12M 25/02* (2013.01);
(Continued)

(58) Field of Classification Search
CPC ............. B01L 5/508; B01L 2200/0689; B01L 2300/0809; B01L 2300/0851; C12Q 1/04; C12M 23/10; C12M 25/02; G01N 2001/28
(Continued)

(56) References Cited

U.S. PATENT DOCUMENTS

| 5,232,838 A | 8/1993 | Nelson et al. |
| 2010/0028933 A1 | 2/2010 | Pflanz |
| 2012/0015394 A1 | 1/2012 | Pflanz et al. |

FOREIGN PATENT DOCUMENTS

| DE | 20 2009 016 410 | 4/2010 |
| EP | 0 816 513 | 1/1998 |

(Continued)

OTHER PUBLICATIONS

Ochoa-Tapia J. Momentum transfer at the boundary between a porous medium and a homogeneous fluid—I. theoretical development. Int. J. Heat Mass Transfer. 1995;38(14):2635-2646.*

(Continued)

*Primary Examiner* — Michael L Hobbs
(74) *Attorney, Agent, or Firm* — Gerald E. Hespos; Michael J. Porco; Matthew T. Hespos

(57) ABSTRACT

An apparatus (1) for analyzing a contaminated surface has a transfer device (2) with a mount (3) and a porous disk-shaped medium (5) having a contact side (6) arrangeable on the contaminated surface. The mount (3) is bindable to the medium on its side (8) facing away from the contact side (6) via a first fixing edge (7a). An analytical device (11) is bindable to the medium (5) on its contact side (6) via a second fixing edge (7b) to remove the medium (5) from the mount (3). The first fixing edge (7a) is bindable to the medium (5) via a first adhesive bond and the second fixing edge (7b) is bindable to the medium (5) via a second (Continued)

adhesive bond. The first adhesive bond is breakable by a lower application of force than the second adhesive bond.

19 Claims, 4 Drawing Sheets

(51) Int. Cl.
*C12M 1/22* (2006.01)
*C12M 1/12* (2006.01)
*G01N 1/02* (2006.01)

(52) U.S. Cl.
CPC ............. *B01L 2200/0689* (2013.01); *B01L 2300/0809* (2013.01); *B01L 2300/0851* (2013.01); *G01N 2001/028* (2013.01)

(58) Field of Classification Search
USPC ..................................... 435/34, 287.1, 287.7
See application file for complete search history.

(56) References Cited

FOREIGN PATENT DOCUMENTS

| | | |
|---|---|---|
| GB | 2 019 434 | 10/1979 |
| JP | 2007-135542 | 6/2007 |
| JP | 2008-193919 | 8/2008 |
| WO | 2008/113444 | 9/2008 |
| WO | WO2008/113444 A1 * | 9/2008 ............ C12M 23/10 |

OTHER PUBLICATIONS

Machine Translation of JP2008-193919. Translated on Nov. 6, 2013.*
M. Pitzurra et al., Hygiene & Medizin, 22 (2) 1997, pp. 77-92.
International Search Report dated Sep. 28, 2011.
English Translation of the IPRP Chapter I PCT.

* cited by examiner

APPARATUS AND METHOD FOR ANALYZING A CONTAMINATED SURFACE

BACKGROUND OF THE INVENTION

1. Field of the Invention

The invention relates to an apparatus for analyzing a contaminated surface comprising a transfer device having a porous disk-shaped medium and comprising an analytical device. The invention further relates to a method for analyzing a contaminated surface using the aforementioned apparatus.

2. Description of the Related Art

Various analytical methods have been established in the analysis of contaminated surfaces.

U.S. Pat. No. 5,232,838 discloses a mount composed of a self-supporting support layer to which a water-soluble adhesive layer is applied. A water-soluble "instant" powder which forms a culture medium for microorganisms upon contact with water is sprinkled in turn onto the adhesive layer. This layered structure is covered by a peelable protective film. After peeling off the protective film, the adhesive layer containing the "instant" powder can be pressed onto a contaminated surface in order to bring the microbes from the surface onto the mount. Subsequently, the affixed "instant" powder is contacted with water in order to initiate the culturing of the microorganisms by the culture medium formed from the "instant" powder.

GB 2 019 434 A discloses an adhesive film in which a porous supporting layer composed of cellulose ester derivatives is coated with an adhesive layer composed of, for example, polyvinylpyrrolidone, polyethylene glycol or polyvinyl methyl ether. The supporting layer can be mechanically stabilized on its side facing away from the adhesive layer by a porous peelable foam layer which facilitates the pressing of the adhesive film onto a microbe-contaminated surface. After removal of the adhesive film from the contaminated surface, the film is placed down on a culture medium with the side facing away from the adhesive layer in order to culture the captured microorganisms.

EP 0 816 513 B1 discloses adhesive films consisting of a water-permeable, but microbe-impermeable, membrane to which an adhesive layer composed of a water-soluble polymer is applied, said adhesive layer being able to fix microbes. The membrane can optionally be applied to a supporting layer. Using these films, microorganisms can be removed from contaminated surfaces by means of the adhesive layer. The film, which can be present in the form of a filter circle, can then be introduced into a filtration unit and be contacted with an aqueous solution containing a staining (chromogenic) substance for the microorganisms. The water-soluble polymer dissolves and passes, with the aqueous solution, the membrane, whereas the microbes are retained on the membrane surface on which the adhesive layer was once situated in order to be subsequently analyzed.

Also widespread is the use of special swabs. These are rods comprising, at one end, a porous thickening with which the surfaces to be tested are intensively rubbed and which are then washed out in subsequent analytical steps in order to test the adherent contamination.

Said swabs are used for all types of surface analyses, whether it be for (bio)chemical methods, for example for DNA analysis, or else for microbiological tests for determining surface contamination.

For the quantitative and semiquantitative determination of surface contamination, it is necessary to detach adherent microorganisms from the swab as quantitatively as possible in order not to falsify the subsequent further test steps. Direct transfer into a culture medium with subsequent testing for growth after incubation is adequate only when checking the sterility of a surface.

The transfer step is never completely achieved and this means that quantitative and semiquantitative analyses using such swabs are difficult to validate because, firstly, contamination as described above is not detachable from the swabs in a reliably quantitative manner and, secondly, the size of the sample area is not quantitatively defined by rubbing with swabs.

Therefore, contact agar plates, which allow a direct evaluation of pathogen counts after appropriate incubation, are primarily used for the quantitative determination of surface contamination.

Instead of swabs, cellulose nitrate membranes can also be used for the quantitative determination of surface contamination, since the electrostatically charged membrane surface pulls off pathogens from the surface to be tested and binds them to the membrane surface structure. These membranes can then be transferred to an agar culture medium and can be quantitatively evaluated after incubation analogously to the method using contact agar plates.

M. Pitzurra et al., Hygiene & Medizin, 22 (2) 1997, 77-92, mhp-Verlag, disclose said method using cellulose nitrate membranes compared to methods using contact agar plates or swabs and to a wash-off method.

The method disclosed by M. Pitzurra et al. has the advantage that the surfaces are not soiled by moist growth or culture medium, as occurs when using contact agar plates, and that the method, compared to swabs, allows direct quantitative evaluation.

In addition, for the area of filtration-based pathogen count determination, a plurality of quick methods are available for liquids, and so the membranes can be directly introduced to these methods after sampling.

Despite the aforementioned advantages with respect to swabs and contact agar plates, said method tested by Pitzurra et al. has so far not been established, since the required sterile handling of the fragile membranes, which typically have a diameter of about 50 mm and a thickness of 100-200 µm, is very laborious and, in terms of the method, not robust. Thus, sampling is very time-consuming and requires attention when removing the membrane from the surface to be analyzed and when further treating the membrane. Also, this method requires the manipulation of the fragile membrane with further technical aids, for example tweezers. The results can be compromised by contamination. These disadvantages also hamper, in particular, reproducible sampling, as required by GLP ("Good Laboratory Practice") and GMP ("Good Manufacturing Practice") regulations for the pharmaceutical industry.

WO 2008/113444 A1 discloses a culture media unit for removing a filter from a filter support device of a filtration apparatus. The culture media unit comprises a bottom part filled with culture medium and a lid.

The lid has a fixing edge which projects into the bottom part and which is bindable to an edge of the filter via an adhesive bond with the filter in order to remove the filter from the filtration apparatus. Said lid makes it possible, without using tweezers or other aids, to transfer the filter from the filter support device into the culture media unit solely by means of the fixing edge of the lid.

The described unit is suitable for microbiological testing of liquid samples after preceding filtration.

DE 20 2009 016 410 U1 discloses a transfer unit for microbiological analysis for accommodating a porous, disk-shaped medium, which transfer unit can remove the medium, by means of a fixing edge, from a first treatment apparatus via the edge of the medium and which transfer unit has an opening which is closable by a removable lid and via which it is possible to carry out subsequent treatment of the medium in a further treatment apparatus.

JP 2008/193919 A discloses a culturing container composed of two book cover-shaped parts joined to one another via a hinge joint, for the analysis of bacterial contamination on surfaces. The first part, which acts as the lid of the culturing container, has a circular projection with a planar adhesive coating. The second part, which acts as a bottom part of the culturing container, has a bowl-shaped recess which is fillable with a culture medium for bacteria. The adhesive-coated projection of the lid can be pressed onto a bacterially contaminated surface, and the bacteria are fixed on the projection by means of the adhesive coating. Subsequently, the lid is folded onto the bottom part by means of the hinge joint and the bacteria fixed on the projection contact the culture medium in the bottom part via uniform contact between the projection and the surface of the culture medium.

JP 2007/135542 A discloses a culturing container similar to the aforementioned culturing container of JP 2008/193919 A, having a separate lid and a separate bottom part containing a culture medium for bacteria to be analyzed. The lid, which is removable from the bottom part, has a circular adhesive coating on its inner lid wall, which is facing the culture medium. Bacteria can be removed from a contaminated surface by means of said adhesive coating and, after their fixation on the adhesive layer, the lid is put over the bottom part such that the bacteria-containing adhesive layer of the lid uniformly adheres to the culture media surface in the bottom part.

The two aforementioned apparatuses, which have proved their worth in principle, are not suitable for carrying out an analysis of contaminated surfaces using porous disk-shaped media, for example membrane filters, since the analysis of the bacteria to be tested can be interfered with in an undesired manner by the adhesive from the adhesive coating that is fixing the bacteria.

It is an object of the present invention to provide an apparatus and a method with which it is possible to quantitatively analyze a contaminated surface using mechanically unstable or fragile porous disk-shaped media without using structurally complex systems and without using further technical aids and without breaking or altering the surface to be analyzed of the disk-shaped media after removal from the contaminated surface and before carrying out the analysis.

SUMMARY OF THE INVENTION

An apparatus in accordance with the invention comprises a transfer device having a mount and having a porous disk-shaped medium having a contact side arrangeable on a contaminated surface, wherein the mount is bindable to the medium on its side facing away from the contact side via a first fixing edge, and which comprises an analytical device which is bindable to the medium on its contact side via a second fixing edge in order to remove the medium from the mount, wherein the first fixing edge is bindable to the medium via a first adhesive bond and the second fixing edge is bindable to the medium via a second adhesive bond and wherein the first adhesive bond is breakable by a lower application of force than the second adhesive bond.

In a further preferred embodiment, a supporting layer is arranged between the mount and the medium, wherein the analytical device is bindable to the medium on its contact side via the second fixing edge in order to remove the medium from the supporting layer.

By arranging a supporting layer between the mount and the porous disk-shaped medium, the fragile medium is protected from breakage and surface damage by means of the supporting layer in the transfer device. This arrangement of the porous medium in the transfer device also allows the medium to be placed on the contaminated surface, for analysis, by means of the transfer device—analogous to a stamp—without the influence of further aids on the medium (e.g., manually or using tweezers).

The fact that the first fixing edge is bindable to the medium via a first adhesive bond and the second fixing edge is bindable to the medium via a second adhesive bond and that the first adhesive bond is breakable by a lower application of force than the second adhesive bond result in the following advantages in the handling of the apparatus according to the invention: the transfer device containing the medium can be applied, in a stamp-analogous manner, with its contact side to the surface to be analyzed. Here, the porous medium is fixed, via the first fixing edge, on the mount or on the optionally provided supporting layer of the transfer device. Subsequently, the transfer device of the apparatus according to the invention is raised from the surface and turned over, so that the contact side of the medium, which contains the contamination from the surface, can be bound to the analytical device of the apparatus according to the invention. A second fixing edge of the analytical device then allows the detachment of the medium from the mount or from the optionally provided supporting layer of the transfer device and the fixation of the medium to said second fixing edge without requiring further technical aids for this purpose.

The detachment of the medium from the transfer device by means of the analytical device is possible as a result of the fact that, in order to break the second adhesive bond mediated by the second fixing edge, a greater force has to be applied than for the breaking of the first adhesive bond mediated by the first fixing edge.

For the purposes of the present inventions, the first fixing edge, via which the medium, on its side facing away from the contact side, is bindable to the mount or to the optionally provided supporting layer, is also to be understood to mean equivalent fixing mechanisms, for example a planar adhesive bond or punctate fixations, which allow fixation of the medium on the mount or the supporting layer, provided that the adhesive bond mediated by said planar or punctate fixing mechanisms is breakable by a lower application of force than the adhesive bond mediated by the second fixing edge.

The differing strengths of the two aforementioned adhesive bonds, which are due to the differing forces required in order to break the adhesive bonds, may preferably be set by both adhesive bonds being formed from adhesives which differ in terms of their physical and/or chemical properties and which exert differing adhesion forces on the porous disk-shaped medium.

Alternatively, it is conceivable to use the same adhesive for both adhesive bonds mediated by the first and second fixing edge, but to vary the degree of coverage of said fixing edges with adhesive for the two adhesive bonds, such that, for example, the second fixing edge has a greater effective adhesive area than the first fixing edge.

Also, when using the same adhesive for the first and the second fixing edge, it is possible for the contact side of the porous medium, and the side of the porous medium that is facing away from the contact side, to have surface properties which differ physically or chemically, and so the side of the medium that is facing away from the contact side is fixable to the first fixing edge by an adhesive bond which is breakable by a lower application of force than the second adhesive bond between the second fixing edge and the contact side of the porous medium.

In a further preferred embodiment, the first and the second adhesive bond are temporary or reversible. Firstly, this facilitates the detachment of the medium from the mount or from the optionally provided supporting layer of the transfer device by means of the analytical device and, secondly, it is possible to subsequently remove the medium fixed by the analytical device from the second fixing edge and to subject it to further analytical steps in other treatment devices.

The first and the second fixing edge preferably each have an adhesive layer composed of an adhesive which is a pressure-sensitive dispersion adhesive or is formed from acrylate copolymer microspheres. As a result, wet or moist porous media are also easily fixable to the first fixing edge of the mount or of the supporting layer of the transfer device or to the second fixing edge of the analytical device or pullable from the second fixing edge for subsequent treatments.

The adhesive layers can be applied either to the first and second fixing edge of the transfer device and of the analytical device or to the edges of the porous medium that correspond in each case to said fixing edges.

In a further embodiment of the invention, the adhesives are sterilizable. The adhesives are preferably DNA-free and protein-free and do not exhibit any unspecific reactions with reagents which are used for the rapid analysis of microbial contamination (e.g., antibody-based reagents or reagents which are used for a polymerase chain reaction (PCR reaction)). More particularly, adhesives can be used which exhibit only slight autofluorescence and do not react unspecifically with relevant staining and labeling reagents for the analysis of the contaminated surface. This applies in particular to wavelength ranges of from 400 to 800 nm that are common in the evaluation. Adhesives which do not exhibit any antibiotic, antiviral or fungicidal properties can also be used.

Preferably, the adhesive is applied to the first and/or second fixing edge via a water-soluble intermediate layer. For the testing of wet or moist contaminated surfaces or if the porous medium is prewet with sterile liquid prior to sampling for improved sampling efficiency, the water-soluble intermediate layer is particularly preferably applied to the first fixing edge of the transfer device between said fixing edge and the adhesive, whereas the second fixing edge of the analytical device has no such intermediate layer. In this embodiment, the water-soluble intermediate layer on the first fixing edge gradually dissolves after prolonged contact of the moist, porous medium, reducing the adhesive force mediated by the first fixing edge to almost nothing. Subsequently, the porous medium is easily raisable from the mount or the optionally provided supporting layer of the turned-over transfer device by means of the adhesive bond with the second fixing edge of the analytical device.

Alternatively, only the second fixing edge, but not the first fixing edge, has a water-soluble intermediate layer. This embodiment has the advantage that the porous medium, after its removal from the transfer device and after its fixation to the second fixing edge of the analytical device, can be wet with a liquid which dissolves the water-soluble intermediate layer in a time-delayed manner, and so the porous medium can be easily pulled off from the second fixing edge of the analytical device for subsequent treatments.

In a preferred embodiment, the supporting layer of the transfer device is porous and consists of an elastic polymer foam. This ensures a uniform application of pressure to the surface to be analyzed by means of the porous medium. Particularly preferably, the supporting layer consists of a material which, upon removal of the porous disk-shaped medium from the transfer device by means of the analytical device, does not leave behind any residues on the side facing away from the contact side of the medium.

The use of an elastic polymer foam as a supporting layer has the further advantage that only minimal contact areas with respect to the medium are present, in accordance with the open, porous structure, and thus lower adhesive forces are automatically present compared to smooth, nonporous supporting layers. This can automatically ensure that the first adhesive bond is breakable by a lower application of force than the second adhesive bond between the second fixing edge and the contact side of the medium.

The supporting layer not only binds the mount to the porous medium, but also optimizes the contact owing to its flexibility and depth and allows a uniform contact pressure on the contaminated surface via the contact side of the porous medium.

The supporting layer is preferably tightly bound to the mount and has the same surface geometry as the porous medium.

The supporting layer can, at the level of its thickness, be enclosed by the, for example, tub-shaped mount, producing a trough which is occupied by the supporting layer.

In a further preferred embodiment, the transfer device is formed as a constituent of a culture media container. In this connection, the supporting layer of the transfer device is attached to the bottom side of the culture media container via an irreversible or reversible adhesive bond. On the top side of the culture media container is situated the culture medium, for example a solid culture medium. In this embodiment, the porous medium is transferred from the supporting layer on the bottom side of the culture media container to the analytical device by means of the transfer device, wherein the first adhesive bond, as described above, is breakable by a lower application of force than the second adhesive bond. The analytical device usable for the transfer can be formed such that it simultaneously serves as a lid for the culture media container.

Particularly preferably, the supporting layer is soaked with an analytical liquid or with a treatment liquid for subsequent treatment of the porous medium. This embodiment has proved its worth in particular when the mount is formed as a tub for the porous supporting layer, and so the mount can be filled with the aforementioned liquids and thus, for example, a direct incubation of pathogens transferred onto the porous medium becomes possible following the supply of liquid. Suitable analytical and treatment liquids are known in microbiology.

In a further preferred embodiment, the disk-shaped porous medium is a membrane filter. When using a porous supporting layer soaked with analytical or treatment liquid (e.g., culture media), the supporting layer and its binding to the membrane filter via the first fixing edge should ensure optimized diffusion and supply of the culture media for the direct evaluation of the pathogens. For this application, it is advantageous when the area of the membrane filter is sized slightly smaller in diameter than the area of the supporting layer, and so, when soaking the supporting layer with the culture medium, the displaced air can escape at the sides.

The transfer unit of the apparatus according to the invention preferably has a cylindrical geometry, but is not restricted to said geometry, since further corresponding units for subsequent treatment may require other geometries.

In a particularly preferred embodiment of the apparatus according to the invention, the second fixing edge of the analytical device is formed by a free end face of an annular wall which is arranged on an inner lid surface of the analytical device.

By means of this embodiment, the porous medium is raisable from the mount or from the supporting layer, optionally provided between mount and medium, of the transfer device by means of the second fixing edge of the analytical device after surface analysis has been carried out because the adhesive force mediated by the second fixing edge exceeds the adhesive force exerted on the medium by the first fixing edge of the transfer device.

The analytical device is, in its circumferential contour, functionally matched to the contour or structure of the transfer device such that the second fixing edge is bindable, by means of an adhesive bond, to the medium only in its peripheral, annular region. Said peripheral region is not usable for further analysis. Thus, in this embodiment, the inner diameter of the second fixing edge of the analytical device specifies the effective surface area of the porous medium that is accessible for analysis. Contamination in said edge region is not taken into consideration in the analysis.

In an alternative preferred embodiment, the analytical device has an opening which is closable by a removable lid and via which it is possible to carry out subsequent treatment of the porous medium. Said closable opening makes it possible to further analyze the contact side of the porous medium that contains the contamination or to contact further treatment devices, which are insertable into said opening, with the contact side.

The invention relates to a method for analyzing a contaminated surface. The method comprises the following steps:

A) arranging the contact side of the porous disk-shaped medium of the transfer device on the contaminated surface, wherein the medium, on its side facing away from the contact side, is bound to the mount of the transfer device via the first fixing edge, B) capturing contamination of the contaminated surface in the medium via the contact side, C) removing the transfer device with the contamination-containing medium from the contaminated surface, D) binding the contact side of the contamination-containing medium in the transfer device to the analytical device via the second fixing edge, E) detaching from the mount of the transfer device the medium bound, as per step D), to the analytical device via the contact side, and F) analyzing the contamination-containing medium which is bound to the analytical device, wherein the detachment in step E) is caused by an adhesive bond which is mediated by the second fixing edge and which exerts a greater adhesive force on the medium than an adhesive bond mediated by the first fixing edge.

Because the detachment in step E) is caused by an adhesive bond which is mediated by the second fixing edge and which exerts a greater adhesive force on the medium than an adhesive bond mediated by the first fixing edge, it is possible to pull off the porous medium from the first fixing edge of the transfer device after the contaminated surface has been analyzed and, at the same time, to fix it to the second fixing edge of the analytical device without requiring additional technical aids (e.g., tweezers, fingers) for said transfer of the porous medium from the contaminated surface into the analytical device.

In an alternative embodiment of the method, between the mount and the medium is arranged a porous supporting layer which, before step A) or after step B), is soaked with an analytical liquid or with a treatment liquid for subsequent treatment of the medium.

Particularly preferably, the porous medium used for the method according to the invention is a membrane filter. The contamination preferably comprises microbes, such as bacteria or fungi. Particularly preferably, the membrane filter is a microporous membrane retaining the aforementioned microbes.

In a further preferred embodiment of the method, in step F), the porous medium bound to the analytical device via the second fixing edge is additionally placed on the surface of a solid culture medium in the bottom part of a culture media container.

The analytical device with the medium fixed to the second fixing edge can be placed down on the surface of a solid culture medium (e.g., agar) arranged in the bottom part of the culture media unit (e.g., Petri dish), for incubation, such that the bottom part of the culture media unit is covered by the analytical device acting as a lid.

A further preferred embodiment combines the function of the transfer device with that of a bottom part of a culture media container and the function of the analytical device as a lid of the culture media container such that the transfer device, on the side opposing the porous medium, is formed as a constituent of the bottom part of the culture media container.

In this connection, the supporting layer of the transfer device is attached to the bottom side of the culture media container via an either irreversible or reversible adhesive bond. On the top side of the culture media container is situated the culture medium, for example a solid culture medium. In this embodiment, the porous medium is transferred from the supporting layer on the bottom side of the culture media container to the analytical device by the porous medium being detached from the supporting layer and being fixed to the second fixing edge by means of the second fixing edge of the analytical device, and subsequently the porous medium comes to rest on the top side of the culture medium and the analytical device covers the culture medium as a lid of the culture media container.

Further features of the invention will be apparent from the following detailed description and the enclosed drawings, in which preferred embodiments of the invention are illustrated by way of example.

DETAILED DESCRIPTION OF THE PREFERRED EMBODIMENTS

Figure 1:
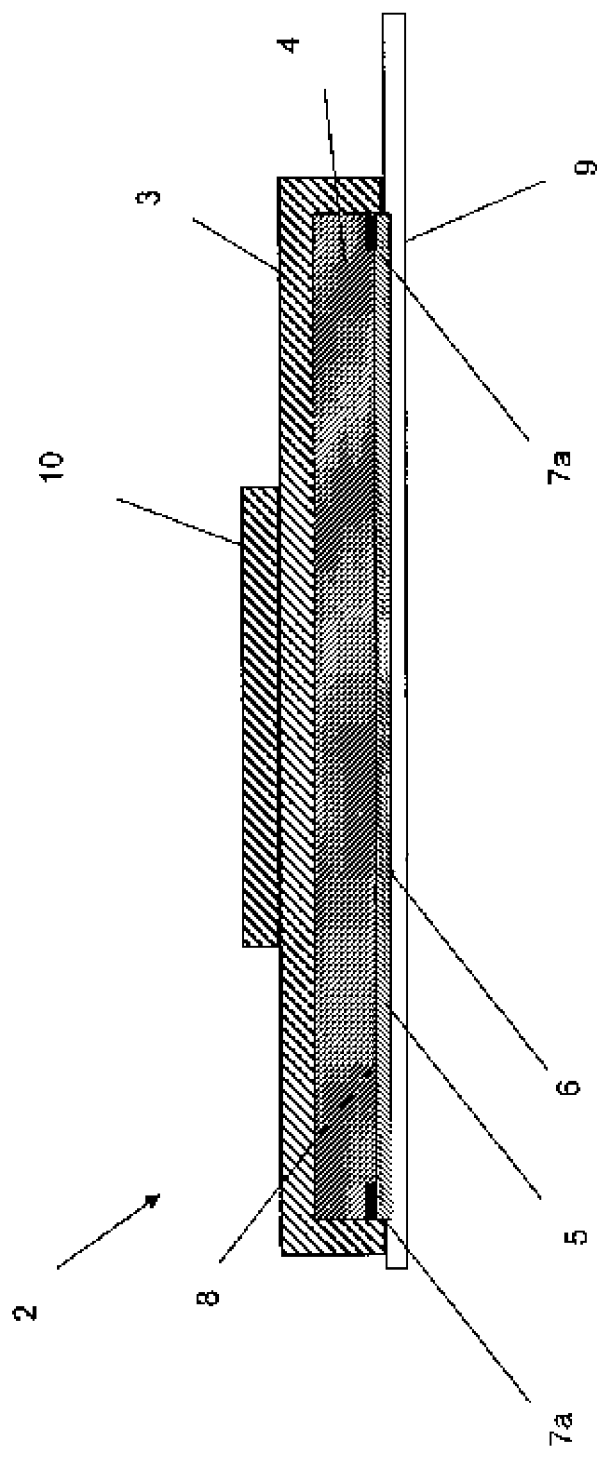
FIG. 1 a sectional side view of a transfer device of the apparatus according to the invention.

As per FIG. 1, the apparatus 1 according to the invention comprises a transfer device 2 having a mount 3 which is particularly preferably formed as a trough in which the supporting layer 4 is arranged. The transfer device 2 also has a porous, disk-shaped medium 5 having a contact side 6. The supporting layer 4 is bindable, via a first fixing edge 7a, to the side 8 of the medium 5 that is facing away from the contact side 6. The first fixing edge 7a is an adhesive bond which ensures that the medium 5, in its edge region, remains adherent to the supporting layer 4. The supporting layer 4 uniformly supports the porous medium 5 on its side 8 facing away from the contact side 6 and protects it from mechanical damage. The supporting layer 4 can be porous and contain an analytical or treatment liquid with which the porous medium 5 is wettable before or during the analysis.

As an optional feature, the transfer device 2 can have a sterile cover 9 in the form of a peelable film having a tab, which film protects the contact side 6 of the porous medium 5 from damage and undesired contamination before analysis of a contaminated surface is carried out. Furthermore, the transfer device can optionally have a handle 10 on the mount 3. The handle 10 facilitates the stamp-analogous handling of the transfer device 2.

The fixing edge 7a is also to be understood here to mean equivalent fixing mechanisms which deviate from an edge-shaped embodiment and which allow a uniform or punctate fixation of the medium 5 to the bottom side of the supporting layer 4.

The uniform design of the fixing edge 7a across the entire bottom side of the supporting layer 4 is particularly appropriate when the supporting layer 4 used is a porous polymer foam. Owing to the minimal contact points of the cell walls of the polymer foam with respect to the medium 5, even an adhesive bond in terms of a fixing edge 7a that is implemented across the entire bottom side of the supporting layer 4 can mediate a lower adhesive force than the adhesive force which is mediated by the second, preferably annular fixing edge 7b.

To carry out an analysis of a contaminated surface, the sterile cover 9, if applicable, is firstly removed from the contact side 6. Using the optional handle 10, the transfer device 2 with the exposed contact side 6 can then be placed, like a stamp, on the contaminated surface to be analyzed, with the contact side 6 of the porous medium 5 coming to rest uniformly on the contaminated surface and the contamination (e.g., microbes) being captured by the porous medium 5 via the contact side 6.

After the transfer device 2 has acted on the surface to be analyzed, the transfer device 2 is raised from the surface and turned over.

Figure 2:
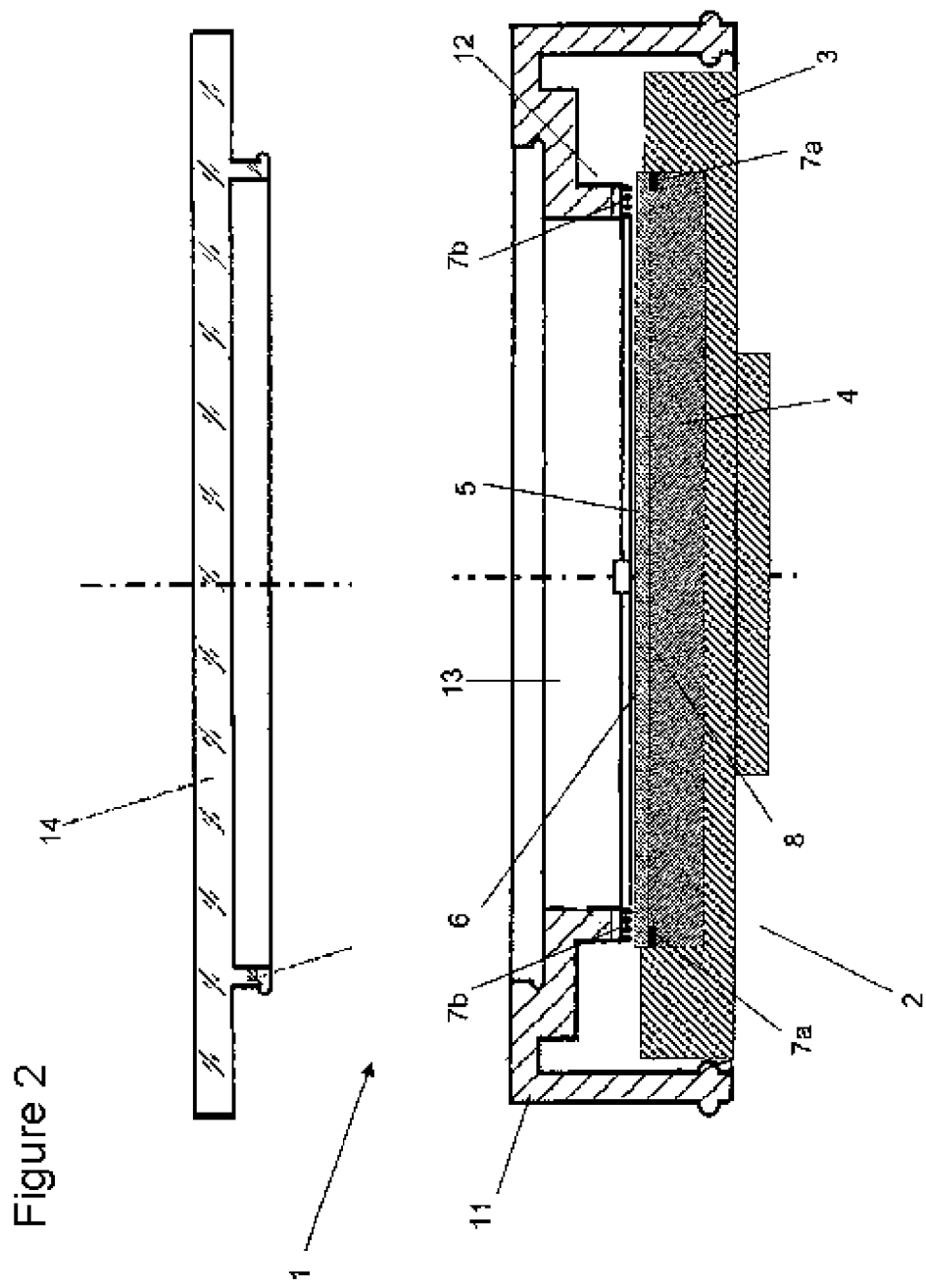
FIG. 2 a sectional side view of the apparatus according to the invention with the transfer device of FIG. 1 and with an analytical device placed on the transfer device.

As per FIG. 2, after the transfer device has been raised and turned over, it is bound to the analytical device 11 such that the edge of the contact side 6 of the medium 5 comes to rest on the second fixing edge 7b of the analytical device 11. Said second fixing edge 7b is formed as an adhesive bond, like the first fixing edge 7a. However, said adhesive bond by means of the second fixing edge 7b is, compared to the adhesive bond by means of the first fixing edge 7a, formed such that the second fixing edge 7b exerts a greater adhesive force on the contact side 6 of the medium 5 than the first fixing edge 7a does on the side 8 of the medium 5 that is facing away from the contact side 6. This variance in the two adhesive forces can, for example,—as indicated examplarily in FIG. 2—be set by the width of the fixing edges comprising the adhesive layer, the same adhesive being used for both adhesive layers. Here, the fixing edge 7b is wider than the fixing edge 7a.

Alternatively, this variance of the adhesive forces exerted by the first and second fixing edge is also possible by the same adhesive at the same adhesive layer width being used in each case for both fixing edges, the surface properties of the contact side 6 of the porous medium 5 and of the side 8 of the porous medium 5 that is facing away from said contact side, however, differing physically or chemically from one another such that both sides 6 and 8 adhere with differing strengths to the fixing edges 7b and 7a, respectively.

In a further embodiment of the apparatus 1 according to the invention, chemically or physically different adhesives are used in each case as adhesive layer for the first and second fixing edge 7a and 7b, which exert adhesive forces of differing strength on the contact side 8 and the side 6 facing away from said contact side.

Because the second fixing edge 7b exerts a stronger adhesive force on the porous medium 5 than the first fixing edge 7a, the medium 5 can be detached from the supporting layer 4 of the transfer device 2 by means of the fixing edge 7b of the analytical device 11 without the use of further aids.

In the embodiment according to FIG. 2, the second fixing edge 7b is formed by a free end face of an annular wall 12.

During the detachment procedure, the transfer device 2 can be reversibly bound to the analytical device 11 by means of a snap connection, clamping connection, snap-in connection or bayonet connection which runs around the mount 3, and which is not shown.

After the porous medium 5 has bound, on its contact side 6, to the analytical device 11 via the second fixing edge 7b, the analytical device 11 can be separated from the transfer device 2. As per FIG. 2, the analytical device 11 can have an opening 13 which is closable by a lid 14. This makes it possible to carry out subsequent treatments on the contact side 6 of the medium 5 that is facing the opening 13.

Figure 3:
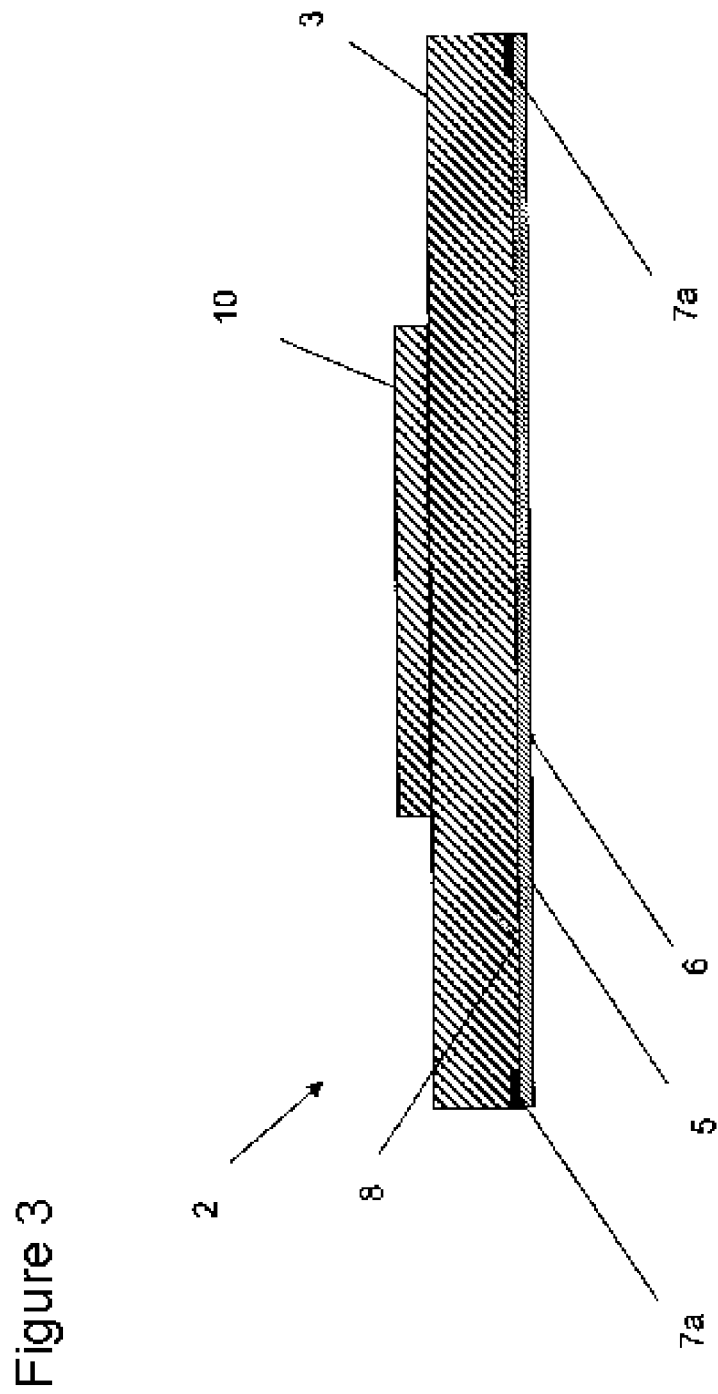
FIG. 3 a sectional side view of a further embodiment of the transfer device of the apparatus according to the invention.

Alternatively, as per the embodiment of the transfer unit 2 that is shown in FIG. 3, it is conceivable for the supporting layer 4 depicted in FIG. 2 to be dispensed with and, in this embodiment, for the medium 5 to be directly and immediately bindable in a uniform manner via the fixing edge 7a to the bottom side of the mount 3 that is facing away from the handle 10, with the medium 5 being mechanically supported by the bottom side of the mount 3.

In the embodiment of the transfer unit 2 that is depicted in FIG. 3, the mount 3 simultaneously acts as a supporting layer for the medium 5. The transfer device 3 has a porous, disk-shaped medium 5 having a contact side 6. The mount 3 is directly and immediately bindable via a first fixing edge 7a to the side 8 of the medium 5 that is facing away from the contact side 6. The first fixing edge 7a is an adhesive bond which ensures that the medium 5, in its edge region, remains adherent to the bottom side of the mount 3 for at least the duration of the contact of the medium 5 with the contaminated surface. The mount 3 uniformly supports the porous medium 5 on its side 8 facing away from the contact side 6 and protects it from mechanical damage. Handling aids, such as an optional handle 10, facilitate the stamp-analogous handling of the transfer device 2.

In the embodiment according to FIG. 3, the fixing edge 7a is also to be understood according to the invention to mean equivalent fixing mechanisms which deviate from an edge-shaped embodiment and which allow a uniform or punctate fixation of the medium 5 to the bottom side of the mount 3.

The uniform design of the fixing edge 7a across the entire bottom side of the mount 3 that is facing away from the handle 10 is particularly appropriate when the mount 3 used is a porous, mechanically stable, preferably incompressible polymer foam. Owing to the minimal contact points of the cell walls of the polymer foam with respect to the medium 5, even an adhesive bond in terms of a fixing edge 7a that is implemented across the entire bottom side of the mount 3 can mediate a lower adhesive force than the adhesive force which is mediated by the second, preferably annular fixing edge 7b.

Figure 4:
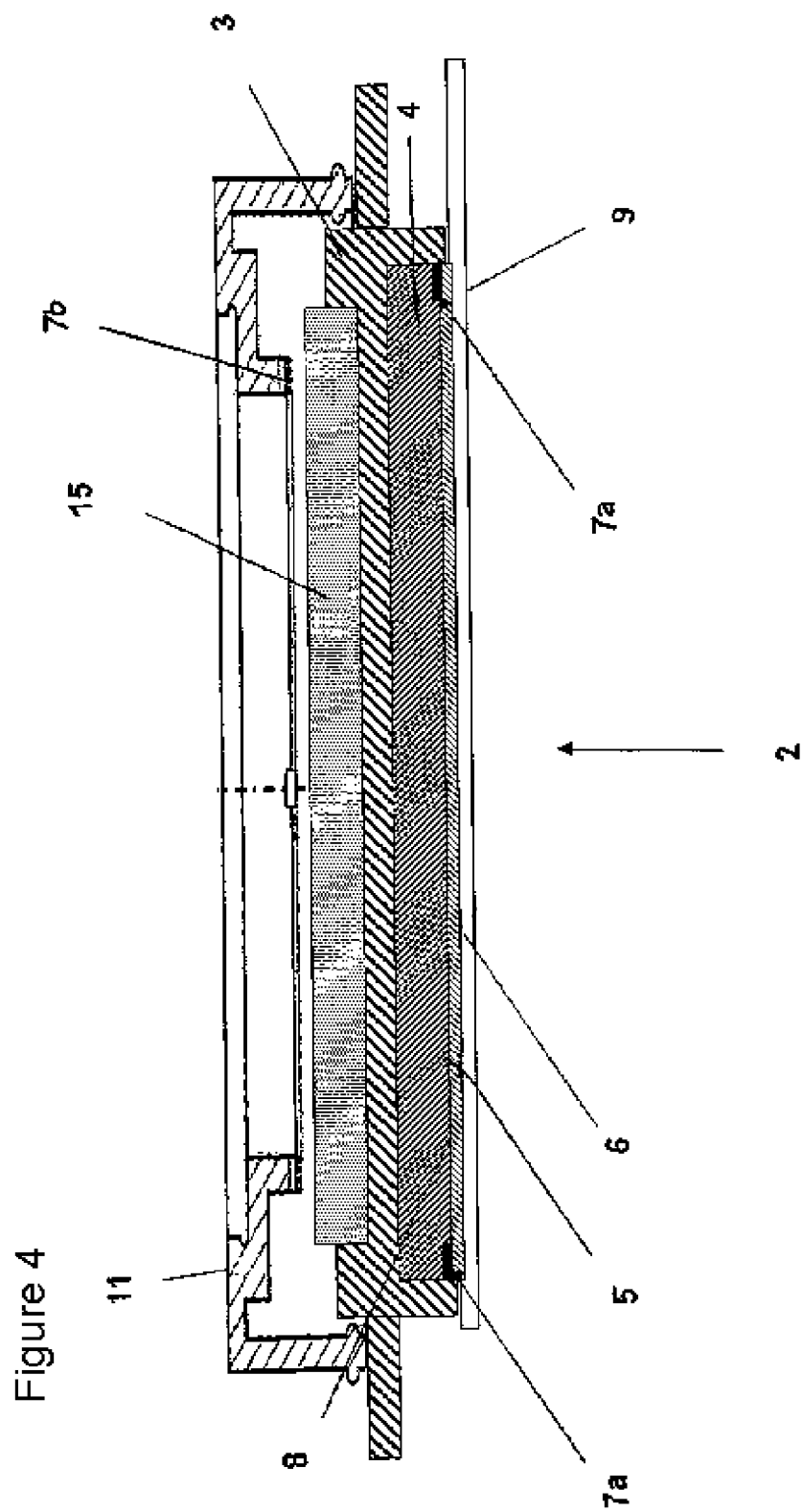
FIG. 4 a side view of a further embodiment of the apparatus according to the invention with the transfer device according to FIG. 1, which is formed as a constituent of a bottom part of a culture media container, wherein the analytical device forms the lid of the culture media container.

In a further embodiment as per FIG. 4, it is possible to use the analytical device 11 as a lid for a bottom part of a culture media container containing a solid culture medium 15. In this case, the bottom part preferably has an inner wall, which is not shown, which corresponds to the second fixing edge 7b of the analytical device 11.

The analytical device 11 can, with the medium 5 fixed to the second fixing edge 7b, be placed on the bottom part of the culture media container, with the side 8 of the medium 5 that is facing away from the contact side 6 coming to rest uniformly on the surface of the solid culture medium. FIG. 4 depicts a culture media container which is ready for use for surface analysis and in which the porous medium 5 is fixed on the supporting layer 4, which is part of the bottom part of the culture media container, on the side facing away from the solid culture medium 15 and is protected by a sterile cover 9.

As per this embodiment of FIG. 4, the transfer device 2 is formed as a constituent of the bottom part of a culture media container. In this case, the top side of the bottom part of the culture media container has an accommodation mechanism for the solid culture medium 15. In this embodiment, the analytical device 11 simultaneously acts as a lid of the culture media container. In this case, the mount 3 of the transfer device 2 is simultaneously the container for the solid culture medium 15, which is covered by the analytical device 11 as a top part of the culture media container and corresponds in dimensions to the analytical device 11.

The invention claimed is:

1. An apparatus (1) for analyzing a contaminated surface, comprising:
    a porous disk-shaped medium (5) having a contact side (6) arrangeable on the contaminated surface and a non-contact side (8) facing away from the contact side (6) to define a first adhesive bond with a first adhesive bonding force,
    a transfer device (2) having a mount (3) with a first fixing edge (7a) adhesively bonded to the non-contact side (8) of the porous disk-shaped medium (5) facing away from the contact side (6) to define a first adhesive bond with a first adhesive bonding force, and
    an analytical device (11) having a second fixing edge (7b) adhesively bonded to the contact side (6) of the medium (5) to define a second adhesive bond with a second adhesive bonding force,
    wherein the first adhesive bonding force is less than the second adhesive bonding force so that the adhesive bond of the mount (3) to the non-contact side (8) of the porous disk-shaped medium (5) is breakable by moving the analytical device (11) away from the transfer device (2) to remove the medium (5) from the mount (3).

2. The apparatus (1) of claim 1, further comprising a supporting layer (4) between the mount (3) and the medium (5) and wherein the analytical device (11) removes the medium (5) from the supporting layer (4).

3. The apparatus (1) of claim 2, wherein the first and the second adhesive bond are temporary or reversible.

4. The apparatus (1) of claim 2, wherein the first and second fixing edges (7a, 7b) each have an adhesive layer composed of an adhesive that is a pressure-sensitive dispersion adhesive or is formed from acrylate copolymer microspheres.

5. The apparatus (1) of claim 4, wherein the adhesive is applied to at least one of the first and second fixing edges (7a, 7b) via a water-soluble intermediate layer.

6. The apparatus (1) of claim 2, wherein the supporting layer (4) is porous and comprises of an elastic polymer foam.

7. The apparatus (1) of claim 6, wherein the supporting layer (4) is soaked with an analytical liquid or with a treatment liquid for subsequent treatment of the porous medium (5).

8. The apparatus (1) of claim 1, wherein the second fixing edge (7b) is formed by a free end face of an annular wall (12) which is arranged on an inner lid surface of the analytical device (11).

9. The apparatus (1) of claim 1, wherein the analytical device (11) has an opening (13) that is closable by a removable lid (14) and via which it is possible to carry out subsequent treatment of the medium (5).

10. The apparatus (1) of claim 2, wherein the transfer device (2) is a constituent of a culture media container, wherein the supporting layer (4) of the transfer device (2) is attached to a bottom side of the culture media container via an irreversible or reversible adhesive bond.

11. A method for analyzing a contaminated surface using the apparatus (1) of claim 1, comprising the steps of:
    A) arranging the contact side (6) of the porous disk-shaped medium (5) of the transfer device (2) on the contaminated surface, wherein the medium (5), on its side (8) facing away from the contact side (6), is bound to the mount (3) of the transfer device (2) via the first fixing edge (7a),
    B) capturing contamination of the contaminated surface in the medium (5) via the contact side (6),
    C) removing the transfer device (2) with the contamination-containing medium (5) from the contaminated surface,
    D) binding the contact side (6) of the contamination-containing medium (5) in the transfer device (2) to the analytical device (11) via the second fixing edge (7b),
    E) detaching from the mount (3) of the transfer device (2) the medium (5) bound, as per step D), to the analytical device (11) via the contact side (6), and
    F) analyzing the contamination-containing medium (5) which is bound to the analytical device (11),
    wherein the detachment in step E) is caused by an adhesive bond which is mediated by the second fixing edge (7b) and which exerts a greater adhesive force on the medium (5) than an adhesive bond mediated by the first fixing edge (7a).

12. The method of claim 11, wherein between the mount (3) and the medium (5) is arranged a porous supporting layer (4) which, before step A) or after step B), is soaked with an analytical liquid or with a treatment liquid for subsequent treatment of the medium.

13. The method of claim 11, wherein the porous medium (5) used is a membrane filter and the contamination comprises microbes.

14. The method of claim 13, wherein, in step F), the porous medium (5) bound to the analytical device (11) via the second fixing edge (7b) is additionally placed on the surface of a solid culture medium in a bottom part of a culture media container.

15. An apparatus (1) for analyzing a contaminated surface, comprising:
- a porous disk-shaped medium (5) having opposite first and second sides (6, 8) and an outer periphery;
- a transfer device (2) having a mount (3) with a first fixing edge (7a) having a first adhesive thereon, the first fixing edge (7a) being dimensioned and configured to engage the first side of the porous disk-shaped medium (5) in proximity to the outer periphery thereof so that the first adhesive adhesively engages the porous disk-shaped medium (5) with a first adhesive force; and
- an analytical device (11) removably mounted to the transfer device (2), the analytical device (11) having a second fixing edge (7b) with a second adhesive thereon, the second fixing edge (7b) being dimensioned and configured to engage the second side of the porous disk-shaped medium (5) in proximity to the outer periphery thereof so that the second adhesive adhesively engages the porous disk-shaped medium (5) with a second adhesive force that exceeds the first adhesive force, wherein the analytical device (11) can remove the medium (5) from the mount (3) by removing the analytical device (11) from the transfer device (2).

16. The apparatus (1) of claim 15, wherein the first and second adhesives are identical, and the second fixing edge (7b) defines a larger contact area than the first fixing edge (7a) so that the second adhesive force that exceeds the first adhesive force.

17. The apparatus (1) of claim 15, wherein the first and second adhesives are different from one another and are selected so that the second adhesive force that exceeds the first adhesive force.

18. The apparatus (1) of claim 15, further comprising a supporting layer (4) between the mount (3) and the medium (5) and wherein the analytical device (11) removes the medium (5) from the supporting layer (4).

19. The apparatus (1) of claim 15, further comprising a sterile cover removable disposed on the mount (3) and covering the medium (5).

* * * * *